United States Patent [19]

O'Mahony et al.

[11] Patent Number: 5,064,844

[45] Date of Patent: Nov. 12, 1991

[54] 1,2,3-TRIAZOLE INSECTICIDES

[75] Inventors: Mary J. O'Mahony, Duxford; Robert J. Willis, Fulbourn, both of England

[73] Assignee: Schering Agrochemicals Limited, England

[21] Appl. No.: 376,990

[22] Filed: Jul. 7, 1989

[30] Foreign Application Priority Data

Jul. 8, 1988 [GB] United Kingdom ............... 8816280
Dec. 3, 1988 [GB] United Kingdom ............... 8828290

[51] Int. Cl.$^5$ ................. A01N 43/647; C07D 249/04
[52] U.S. Cl. .................................... 514/359; 548/255
[58] Field of Search ...................... 548/255; 514/359

[56] References Cited

U.S. PATENT DOCUMENTS 4,499,280 2/1985 Reisser .............................. 548/255

FOREIGN PATENT DOCUMENTS 1542769 7/1969 Fed. Rep. of Germany .
2442685 3/1975 Fed. Rep. of Germany ...... 548/255
2442843 3/1975 Fed. Rep. of Germany ...... 548/255

OTHER PUBLICATIONS

Swartz, et al., "Synthesis of Some 4-Substituted-2-(o-halogenophenyl)-1,2,3-triazoles", J. Hetero. Chem. (1983), 20 (6), pp. 1561-1564.

Peter N. Neuman, "Nitro Derivatives of Phenyl-1,2,3-triazole(1)", J. Hetero. Chem. (1971), 8(1), pp. 51-56.

*Primary Examiner*—Mary C. Lee
*Assistant Examiner*—Patricia L. Morris
*Attorney, Agent, or Firm*—Ostrolenk, Faber, Gerb & Soffen

[57] ABSTRACT

Compounds of formula I

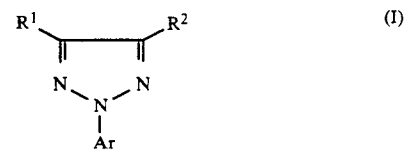

and N-oxides thereof, in which
Ar is aryl;
$R^1$ and $R^2$ are the same or different and are hydrogen, alkyl, alkenyl or alkynyl, each of which is optionally substituted, aryl, heterocyclyl, cyano, halogen, nitro, $XR^3$, $S(O)_2NR^4R^5$, CHO and functional derivatives thereof, $NR^4R^5$ or $CYNR^4R^5$;
$R^3$ is hydrogen or optionally substituted alkyl or alkenyl;
$R^4$ and $R^5$ are the same or different and are hydrogen, optionally substituted alkyl, acyl or aryl, or together with the nitrogen to which they are attached, form a 5 to 7 membered ring which can contain other hetero atoms;
X is O, S, $S(O)_n$, $OSO_2$, YCO or COO;
Y is O or S; and n is 1 or 2; have pesticidal activity and especially insecticidal and acaricidal activity. Many of the compounds are novel.

9 Claims, No Drawings

1,2,3-TRIAZOLE INSECTICIDES

This invention relates to new compounds having pesticidal and especially insecticidal and acaricidal activity.

In Ep 201.852 and a number of subsequent patents, there are claimed insecticidal pyrazoles, in which the pyrazole is substituted in the 1-position by substituted phenyl groups. We have now found that 1,2,3-triazoles. substituted in the 2 position by certain aryl groups, have insecticidal and/or acaricidal activity. The only reference, of which we are aware, which discloses acaricidal 2-aryl-1,2,3-triazoles is DE OLS 1542769. In there are claimed 2-phenyl-4-nitro-1,2,3-triazoles, in which the phenyl is optionally substituted in the meta or para positions by fluoro, chloro or trifluoromethyl. No mention is made of insecticidal activity. The present invention provides a pesticidal composition which comprises a compound of formula I

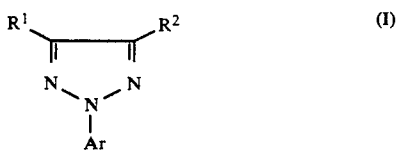

and N-oxides thereof, in which

Ar is aryl;

$R^1$ and $R^2$ are the same or different and are hydrogen. alkyl, alkenyl or alkynyl, each of which is optionally substituted, aryl, heterocyclyl, cyano, halogen, nitro, $XR^3$, $S(O)_2NR^4R^5$, CHO and functional derivatives thereof, $NR^4R^5$ or $R^3$ is hydrogen or optionally substituted alkyl or alkenyl;

$R^4$ and $R^5$ are the same or different and are hydrogen, optionally substituted alkyl, acyl or aryl, or together with the nitrogen to which they are attached, form a 5 to 7 membered ring which can contain other hetero atoms;

X is 0. S. $S(O)_n$, $OSO_2$, YCO or COO;

Y is O or S; and n is 1 or 2; with the proviso that when $R^1$ is hydrogen and $R^2$ is nitro, Ar is phenyl containing at least three substituents.

said compound being in admixture with an agriculturally acceptable diluent or carrier.

The invention also provides a method of combating pest, especially insects or acarids, at a locus infested or liable to be infested therewith, which comprises applying to the locus a compound of formula I, as defined above.

Many of the compounds of formula I are novel and the invention includes all such novel compounds especially compounds where $R^1$ and $R^2$ are as defined above and Ar is (a) 4-trifluoromethylphenyl or 5-trifluoromethyl-2-pyridyl, in which the phenyl or pyridyl is optionally further substituted, or (b) phenyl having at least three substituents. Apart from trifluoromethyl, other substituents include halogen and trifluoromethyloxy, trifluoromethylthio or trifluoromethylsulphonyl.

Alkyl, alkoxy and alkylthio groups are preferably of 1 to 4 carbon atoms. Preferred alkyl groups are methyl or t-butyl. Alkylthio groups are preferably methylthio. Alkenyl or alkynyl groups are generally of 2 to 5 carbon atoms. These groups may be substituted by one or more of the same or different groups such as halogen. $XR^3$ dihalocyclopropyl, cyano, nitro, optionally substituted amino, acyloxy and aryl. Aryl groups are usually phenyl. optionally substituted, e.g, by halogen, alkyl, haloalkyl. alkoxy or nitro. The term aryl may include heteroaryl groups such as imidazolyl, thienyl, furyl or pyridyl. The term 'acyl' includes the residue of sulphonic and phosphorus containing acids as well as carboxylic acids. Acyl groups may be for example alkanoyl, e.g, of 1 to 4 carbon atoms, or alkylsulphonyl or haloalkylsulphonyl. Optionally substituted amino groups are generally of formula $NR^4R^5$ Heterocyclyl groups are generally 4 to 6 membered and can contain various hetero atoms, such as oxygen, nitrogen or sulphur.

When $R^4$ and $R^5$ form a ring this is generally a morpholino or piperidino ring. This ring can carry another fused ring and/or can be substituted, e.g, by one or more optionally substituted alkyl groups. Functional derivatives of CHO include oximes, hydrazones and semicarbazones.

A particularly preferred group of compounds are those where Ar is 2,6-dichloro-4-trifluoromethylphenyl. It is generally preferred that $R^1$ is hydrogen or methyl and $R^2$ is halogen, nitro, cyano, (halo)alkylthio, alkylsulphonyl, alkylsulphinyl, halomethyl or (halo)alkylthiomethyl.

Some novel compounds of formula I have weak pesticidal activity but still have utility as intermediates and such compounds also form one aspect of the invention. Examples of such compounds are those where $R^1$ is hydrogen or methyl and $R^2$ is mercapto, thiocyanato, formyl, carboxy, bromomethyl, carboxymethyl, hydroxymethyl or cyanomethyl.

The compounds of the invention have insecticidal and acaricidal activity and are particularly useful in combating a variety of economically important insects, and acarids including animal ectroparaites, e.g. Lepidoptera, including *Spodoptera littoralis, Heliothis armigera,* and *Pieris brassicase;* Diptera, including *Musca domestics, Ceratitis capitata, Erioischia brassicase, Lucilia sericatea* and *Aedes aegypti;* Homoptera, including aphids such as *Meqoura viciae* and *Nilaparvata lugens;* Coleoptera, including *Phaedon cochleariae, Anthonomus grandis* and corn rootworms (*Diabrotica* spp., eg. *Diabrotics undecimpunctata*); Orthoptera, including *Diabrotica undercimpunctata*); Orthoptera, including *Blattella germanica;* ticks, e.g. *Boophilus microplus* and lice, including *Damalinia bovis* and *Linognathus vituli.*

Some of compounds also have herbicidal activity, against undesirable weeds such as *Polygonum lapathifolium* (Pale persicaria), *Galium aparine* (cleavers), *Chrysanthemum segetum* (corn marigold), *Alopecurus myosuroides* (blackgrass), *Avena fatua* (wild oat), *Abutilon theophrasti* (velvet leat), *Pharbitis purpurea* (morning glory), *Echinochloa crus-galli* (barnyard grass), *Setaria viridis* (green foxtail) and *Solanum nigrum* (black nightshade).

More than one compound of the invention can, of course, be included in the composition.

In addition the composition can comprise one or more additional pesticides for example compounds known to possess herbicidal, fungicidal, insecticidal, acaricidal or nematicidal properties. Alternatively the compounds of the invention can be used in sequence with the other pesticides.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates, e.g, butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g, the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g, sorbitan fatty acid esters, condensation products of such esters with ethylene oxide, e.g, polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such a amine oxide or polyoxyethylene alkylamine; an amide-linked amine prepared by the condensation of a carboxylic acid with a di- or polyamine; or a quaternary ammonium salt.

The compositions of the invention can take any form known, in the art for the formulation of insecticidal compounds. for example, a solution, a dispersion, an aqueous emulsion, a dusting powder, a seed dressing, a fumigant, a smoke, a dispersible powder, an emulsifiable concentrate. granules or baits. Moreover it can be in a suitable form for direct application or as a concentrate or primary composition which requires dilution with a suitable quantity of water or other diluent before application.

As a dispersion, the composition comprises a compound of the invention dispersed in a liquid medium, preferably water. It is often convenient to supply the consumer with a primary composition which can be diluted with water to form a dispersion having the desired concentration. The primary composition can be provided in any one of the following forms. It can be a dispersible solution which comprises a compound of the invention dissolved in a water-miscible solvent with the addition of a dispersing agent. A further alternative comprises a compound of the invention in the form of a finely ground powder in association with a dispersing agent and intimately mixed with water to give a paste or cream which can if desired be added to an emulsion of oil in water to give a dispersion of active ingredient in an aqueous oil emulsion.

An emulsifiable concentrate comprises a compound of the invention dissolved in a water-immiscible solvent together with an emulsifying agent and which is formed into an emulsion on mixing with water.

A dusting powder comprises a compound of the invention intimately mixed with a solid pulverulent diluent, for example, kaolin.

A granular solid comprises a compound of the invention associated with similar diluents to those which may be employed in dusting powders, but the mixture is granulated by known methods. Alternatively it comprises the active ingredient adsorbed or absorbed on a pre-granular diluent. for example. Fuller's earth, attapulgite or limestone grit.

A wettable powder usually comprises the active ingredient in admixture with a suitable surfactant and an inert powder diluent such as china clay.

Another suitable concentrate, particularly when the product is a solid, is a flowable suspension concentrate which is formed by grinding the compound with water, a wetting agent and a suspending agent.

Baits can include an attractant and may comprise a protein hydrolysate e.g, for the control of fruit flies, sugar e.g, for the control of adult Musca spp, or corn cob e.g. for the control of cockroaches.

The concentration of the active ingredient in the composition of the present invention is preferably within the range of 1 to 30 per cent by weight, especially 5 to 30 per cent by weight. In a primary composition the amount of active ingredient can vary widely and can be, for example, from 5 to 95 per cent by weight of the composition.

The compounds of the invention may be prepared by a variety of methods known in the art.

For example:

(a) a compound of formula II

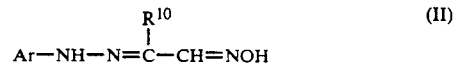

where $R^{10}$ has the same meaning as $R^1$, can be ring closed, under oxidative conditions, eg using a copper salt, lead tetraacetate, bromine. N-halosuccinimide., potassium ferricyanide or dipotassium nitrodisulphonate, to give an N-oxide of a compound of formula I in which $R^2$ is hydrogen. This compound can then be modified in known ways to convert $R^2$ to (b) a compound of formula II, in which $R^{10}$ is nitro, can be ring closed, eg using a base, such as sodium hydroxide, and an acid anhydride, such as acetic anhydride, and the nitro group can be reduced and the subsequent amino group modified in known manner.

(c) a compound of formula III

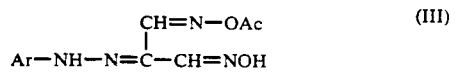

in which Ac is an acyl group can be ring closed, eg using caesium carbonate, followed by hydrolysis to give a compound of formula I in which $R^1$ is hydrogen and $R^2$ is formyl. This group can then be modified in L known manner to give other desired $R^2$ groups.

(d) a compound of formula IV

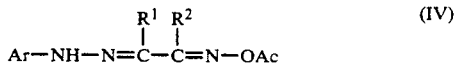

in which Ac is an acyl group can be ring closed, e.q using caesium carbonate.

Thio groups can be converted to sulphinyl and sulphonyl groups by oxidation, e.g, using a suitable peracid.

Other methods will be apparent from the Examples given hereinafter.

The invention is illustrated in the following examples. Structures of isolated novel compounds were confirmed by elemental and/or other appropriate analyses.

EXAMPLE 1

A solution of 2,6-dichloro-4-trifluoromethylphenylhydrazine (10.2 g) in ether (15 ml) was added with cooling to a solution of '2-oxopropanal 1-oxime (3.62 g) in ether (15 ml) at 0°. The mixture was stirred at room temperature overnight and magnesium sulphate and charcoal added. The mixture was filtered and solvent evaporated under reduced pressure. The residue was purified by column chromatography to give 2-(2,6-dichloro-4-trifluoromethylphenylhydrazono)propanal 1-oxime, m.p, c.108°.

To a solution of this product (13.26 g) in pyridine was added, dropwise, copper sulphate (13 g) in water (55 ml) and the mixture stirred at room temperature overnight. It was then cooled, acidified with 25% sulphuric acid and extracted with ether. The extracts were worked up in conventional manner and the product purified by column chromatography to give 2-(2,6-dichloro-4-trifluoromethyl-phenyl)-4-methyl-2H-1,2,3-triazole 1-oxide, m.p. 127°. (Compound 1)

EXAMPLE 2

A solution of Compound 1 (2.8 g) and trimethyloxonium tetrafluoroborate (1.6 g) in dichloromethane (20 ml) was stirred at room temperature for 3 days. Dry ether (40 ml) was added and the solid collected by filtration under nitrogen. It was then dissolved in acetonitrile and potassium cyanide (0.9 g) added and the mixture stirred at room temperature for 5 days. The solvent was evaporated under reduced pressure and the residue extracted with dichloromethane. The extract was evaporated and the residue purified by column chromatography to give 2-(2,6-dichloro-4-trifluoromethylphenyl)-5-methyl-2H-1,2,3-triazole-4-carbonitrile, m.p. 53°. (Compound 2)

EXAMPLE 3

Compound 1 (1.4 g) was treated with trimethyloxonium tetrafluoroborate in a similar manner to Example 2. The product was dissolved in acetonitrile and sodium methanethiolate (0.5 g) added and the mixture stirred at room temperature for 10 minutes. The solvent was evaporated under reduced pressure and the residue extracted with dichloromethane. The extract was evaporated and the residue purified by column chromatography to give 2-(2,6-dichloro-4-trifluoromethylphenyl)-4-methyl-5-methylthio-2H-1,2,3-triazole, m.p. 38°-40°. (Compound 3)

EXAMPLE 4

Bromine (12.5 g) was added over 1 minute to a solution of Compound 1 (6.1 g) in dichloromethane (50 ml) and a solution of sodium carbonate (2.7 g) in water (60 ml). After 5 hours the mixture was quenched with aqueous sodium thiosulphate and stirred overnight. The organic layer was separated, dried over magnesium sulphate and evaporated under reduced pressure. The residue was recrystallised from ethyl acetate/hexane to give 4-bromo-2-(2,6-dichloro-4-trifluoromethylphenyl)-5-methyl-2-1,2,3-triazole 3-oxide, m.p. 115°-116°. A mixture of this compound (2 g) and phosphorus trichloride (1.64 ml) was heated under reflux for 1 hour. Water was added to the mixture and extracted with ether. The extract was washed with brine, dried and evaporated. The residue was recrystallised from hexane to give 4-bromo-2-(2,6-dichloro-4-trifluoromethyl-phenyl)-5-methyl-2H-1,2,3-triazole, m.p. 82°. (Compound 4)

EXAMPLE 5

A mixture of [2-(2,6-dichloro-4-trifluoromethylphenyl)-2H-1,2,3-triazol-4-yl]methyl methanesulphonate (1.83 g). sodium methanethiolate (0.34 g) and acetonitrile (20 ml) was stirred at room temperature for 3½ days, poured into water and extracted with ether. The extract was dried and evaporated and the residue purified by column chromatography to give 2-(2,6-dichloro-4-trifluoro-methylphenyl)-4-(methylthiomethyl)-2H-1,2,3-triazole, mp 65°-67°. (Compound 5)

EXAMPLE 6

2-(2,6-Dichloro-4-trifluoromethylphenyl)-2-1,2,3-triazole-4-carboxaldehyde oxime (26.3 g) was heated under reflux with 1,3,5-trioxane and 2 molar hydrochloric acid (1000 ml). The mixture was extracted with ether and the extract washed with water, dried and evaporated. The residue was purified by column chromatography to give 2-(2,6-dichloro-4-trifluoromethylphenyl)-2H-1,2,3-triazole-4-carboxaldehyde, mp 94°-95°. (Compound 6)

EXAMPLE 7

A mixture of Compound 6 (1.5 g), hydroxylamine hydrochloride (0.4 g), sodium formate (0.66 g) and formic acid (10 ml) was heated under reflux overnight. Water was added and the precipitate filtered and purified by column chromatography to give 2-(2,6-dichloro-4-trifluoromethyl-phenyl)-2H-1,2,3-triazole-4-carbonitrile, mp 51°-53°. (Compound 7)

EXAMPLE 8

A mixture of Compound 6 (3.38 g), sodium methanethiolate (1.8 g) and acetic acid (20 ml) was stirred at room temperature for 1 hour. It was poured into water and extracted with ethyl acetate. The extract was washed with water, dried and evaporated and the residue triturated with light petroleum (40°-60°), filtered and dried to give 2-(2,6-dichloro-4-trifluoromethylphenyl)-4-[di(methylthio)methyl]-2H-1,2,3-triazole, mp 67°-68°. (Compound 8)

EXAMPLE 9

A mixture of Compound 6 (2 g), ethyl triphenylphosphonium bromide (2.4 g), potassium carbonate (1.2 g). 1,4-dioxane (20 ml) and water (0.3 ml) was heated under reflux for 7 hours. It was then stirred at room temperature for 2½ days and heated under reflux for a further 10 hours. Solvent was evaporated under reduced pressure and the residue purified by column chromatography to give 2-(2,6-dichloro-4-trifluoromethylphenyl)-4-(1-propenyl)-2H-1,2,3-triazole. mp 35°. (Compound 9)

EXAMPLE 10

A solution of Compound 6 (2 g), in dichloromethane (5 ml) was added dropwise to a solution of diethylaminosulphur trifluoride (1.04 g) in dichloromethane (5 ml). The mixture was stirred at room temperature for 1 hour and then poured into water and extracted with dichloromethane. The extract was washed with brine, dried and evaporated and the residue was allowed to crystallise on standing to give 2-(2,6-dichloro-4-trifluoromethylphenyl)-4-difluoro-methyl-2H-1,2,3-triazole, mp 36°-37°. (Compound 10)

EXAMPLE 11

A solution of 2,6-dichloro-4-trifluoromethylphenylhydrazine (5 g) in acetic acid was added dropwise to a mixture of 40% aqueous glyoxal (50 ml) and water (400 ml). The mixture was stirred at room temperature for 2 hours and solid collected by filtration. A sample was recrystallised from ethanol to give 2-(2,6-dichloro-4-trifluoromethylphenylhydrazono)acetaldehyde, m.p. 131°-133°. This crude product (2.85 g) in ethanol (30 ml) was added to a solution of hydroxylamine hydrochloride (0.7 g) in water (10 ml), which had been neutralized with sodium acetate (0.82 g). The mixture was stirred at room temperature and then extracted with ethyl acetate. The extract was washed with brine, dried and evaporated to 2-(2,6-dichloro-4-trifluoromethylphenylhydrazono)acetaldehyde oxime. This was then treated with copper sulphate, in a similar manner to Example 1, to give 2-(2,6-dichloro-4-trifluoromethylphenyl)-2H-1,2,3-triazole 1-oxide, m.p. 153°-154°, which in turn was treated with trimethyloxonium tetrafluoroborate and sodium methanethiolate, in a similar manner to Example 3, to give 2-(2,6-dichloro-4-trifluoromethylphenyl)-4-methylthio-2H-1,2,3-triazole, m p. 100°-101°. (Compound 11)

EXAMPLE 12

2,6-Dichloro-4-trifluoromethylaniline (5 g) was diazotised with sodium nitrite and sulphuric acid and the diazonium salt added to a solution of 2-nitroacetaldehyde oxime (2.3 g) and sodium acetate (1.8 g) in water (100 ml). The precipitate was collected by filtration and then extracted with ether. The extract was washed with brine dried and evaporated and the residue purified by column chromatography to give 2-(2,6-dichloro-4-trifluoro-methylphenylhydrazono)-2-nitroacetaldehyde oxime, mp 149°-150°. Acetic anhydride (2 ml) was added slowly to a solution of this product (1 g) in 2M sodium hydroxide (25 ml). The mixture was acidified with hydrochloric acid and extracted with ether. The extract was washed with brine, dried and evaporated and the residue purified by column chromatography, followed by recrystallisation from hexane to give 2-(2,6-dichloro-4-trifluoromethylphenyl)-4-nitro-2H-1,2,3-triazole. m.p. 105°. (Compound 12 )

EXAMPLE 13

A solution of 3-chloroperbenzoic acid (0.84 g) in chloroform (25 ml) was slowly added to a solution of compound 3 (Example 3; 0.8 g) in chloroform (25 ml) which had been cooled to −10°. The mixture was stirred at room temperature overnight and solvent evaporated under reduced pressure. The residue was purified by column chromatography to give 2-(2,6-dichloro-4-trifluoro-methylphenyl)-4-methyl-5-methylsulphonyl-2H-1,2,3-triazole. mp 87°-89°. (Compound 13)

EXAMPLE 14

2-(2,6-Dichloro-4-trifluoromethylphenyl)-2H-1,2,3-triazole-4-carboxylic acid (8.18 g) was treated with thionyl chloride (150 ml) to give crude acid chloride. A solution of this in tetrahydrofuran was added to ammonia with ice cooling. The mixture was stirred at room temperature for one hour, solvent was removed and the product extracted with ethyl acetate and worked up in conventional manner to give 2-(2,6-dichloro-4-trifluoromethylphenyl)-2H-1,2,3-triazole-4-carboxamide, m.p. 239° (Compound 14 ).

EXAMPLE 15

Compound 14 (5.4 q) was reacted with Lawesson's reaqent (2,4-bis(4-methoxyphenyl)-1,2,3,4-dithiadiphosphetane 2,4-disulphide) (3.37 g) in toluene, under reflux, for two hours. Solvent was removed and the residue purified by column chromatography and recrystallisation from light petroleum to give 2-(2,6-dichloro-4-trifluoromethylphenyl)-2H-1,2,3-triazole-4-carbothioamide, mp 214°-217.5°. (Compound 15 )

EXAMPLE 16

A mixture of 4-bromomethyl-2-(2,6-dichloro-4-trifluoro-methylphenyl)-5-methyl-2H-1,2,3-triazole, (2.14 g) and potassium cyanide in dimethyl sulphoxide (20 ml) was stirred at room temperature for 2 hours. The mixture was added to water and extracted with ether. The extract was worked up to give 2-(2,6-dichloro-4-trifluoromethyl-phenyl)-5-methyl-2H-1,2,3-triazol-4-ylacetonitrile, m.p. 103°-104°. (Compound 16)

EXAMPLE 17

A mixture of 4-bromomethyl-2-(2,6-dichloro-4-trifluoro-methylphenyl)-5-methyl-2H-1,2,3-triazole (1 g) and dimethylamine (10 ml of 33% solution in industrial methylated spirits) was stirred for 1 hour at room temperature. It was then evaporated and the residue extracted with ether. The extract was worked up to give 4-(N,N-dimethylaminomethyl)-2-(2,6-dichloro-4-trifluoromethylphenyl)-5-methyl-2H-1,2,3-triazole. mp 67°-68°. (Compound 17)

EXAMPLE 18

A solution of sulphuryl chloride (0.22 ml) in dichloromethane (10 ml) was added dropwise to a refluxing solution of compound 3 (0.96 g) in dichloromethane (10 ml) and the mixture heated under reflux for 4 hours. The solvent was evaporated under reduced pressure and the residue purified by column chromatography to give 2-(2,6-dichloro-4-trifluoromethylphenyl)-4-methyl-5-chloromethylthio-2H-1,2,3-triazole, obtained as an oil. (Compound 18)

EXAMPLE 19

A mixture of [2-(2,6-dichloro-4-trifluoromethylphenyl)-2H-1,2,3-triazol-4-yl]methanol (1.5 g), sodium hydride (0.15 g) and methyl iodide (0.7 g) in tetrahydrofuran (30 ml) was stirred at room temperature for 2 hours and left over the weekend. The mixture was added to water and extracted with ether. The extract was worked up to give 2-(2,6-dichloro-4-trifluoromethylphenyl)-4-methoxymethyl-2H-1,2,3-triazole, m.p. 32°-33°. (Compound 19)

EXAMPLE 20

4-Bromomethyl-2-(2,6-dichloro-4-trifluoromethylphenyl) 2H-1,2,3-triazole (2.9 g) was added portionwise to a stirred mixture of ethanethiol (0.5 g) and sodium hydride (0.25 g) in tetrahydrofuran (30 ml) and the mixture stirred at room temperature for 3 hours. The mixture was added to water and extracted with ether. The extract was worked up to give 2-(2,6-dichloro-4-trifluoromethylphenyl)-4-(ethylthiomethyl)-2H-1,2,3-triazole, m.p. 53°–54°. (Compound 19)

EXAMPLE 21

A mixture of compound 32 (11 g) (see later) and aqueous potassium hydroxide (14.4 g) was stirred at room temperature under nitrogen, for 5 hours. The mixture was added to ice, acidified with sulphuric acid and extracted with ether. The extract was worked up to give 2-(2,6-dichloro-4-trifluoromethylphenyl)-4-mercaptomethyl-2H-1,2,3-triazole.m.p. 58°–60°(Compound 21)

EXAMPLE 22

Chlorodifluoromethane was bubbled through a stirred mixture of compound 21 (2 g), aqueous sodium hydroxide (1.3 g in 15 ml water) and dioxan (20 ml) heated to 65° over 3 hours until the showed complete reaction. The mixture was added to water and extracted with ether. The extract was worked up to give 2-(2,6-dichloro-4-trifluoro-methylphenyl)-4-[(difluoromethylthio)methyl]2H-1,2,3-triazole. m.p. 32°–33°. (Compound 22)

EXAMPLE 23

4-Bromomethyl-2-(2,6-dichloro-4-trifluoromethylphenyl)-2H-1,2,3-triazole (9.55 g), potassium thiocyanate (1 g) and tetrahydrofuran (50 ml) were heated under reflux for 3 hours. The mixture was poured into water, solid collected and recrystallised from ethyl aceteate/hexane to give 2-(2,6-dichloro-4-trifluoromethylphenyl)-4-thiocyanato-methyl-2H-1,2,3-triazole, m.p. 115°–117°. (Compound 23)

EXAMPLE 24

A solution of 2-(2,6-dichloro-4-trifluoromethylphenyl)-2H-1,2,3-triazole-4-carboxaldehyde (3.1 g), in dichloromethane (20 ml) was added to a solution of triphenylphosphonium dibromide at −20° (prepared by mixing a solution of carbon tetrabromide (31.2 g) in dichloromethane (30 ml) with a solution of triphenylphosphine (21 g) in dichloromethane (70 ml)) and the mixture stirred for 1 hour. Hexane was added and the mixture filtered. The filtrate was worked up to give 2-(2,6-dichloro-4-trifluoromethylphenyl)-4-(2.2-dibromo-vinyl)-2H-1,2,3-triazole. 89°–91° . (Compound 24)

EXAMPLE 25

A mixture of compound 17 (5.3 g) and sodium iodide (4.26 g) in acetone (150 ml) was stirred over 6 days. Solvent was removed and the residue dissolved in ether filtered and the filtrate worked up to give 2-(2,6-dichloro-4-trifluoromethylphenyl)-4-methyl-5-iodomethylthio-2H-1,2,3-triazole, obtained as an oil. (Compound 25)

EXAMPLE 26

A mixture of compound 25 (1.5 g) and sodium methoxide (prepared from sodium (0.1 g) and methanol (15 ml)) in tetrahydrofuran (25 ml) was stirred for one day at room temperature. Solvent was removed and the product purified by silica gel column chromatography to give 2-(2,6-dichloro-4-trifluoromethylphenyl)-4-methyl-5-methoxymethylthio-2H-1,2,3-triazole, obtained as an oil. (Compound 26)

EXAMPLE 27

A mixture of compound 25 (2 g) and sodium methanethiolate (0.3 g) in tetrahydrofuran (40 ml) was stirred overnight at room temperature. Solvent was removed and the product purified by silica gel column chromatography to give 2-(2,6-dichloro-4-trifluoromethylphenyl)-4-methyl-5-(methylthiomethylthio)-2H-1,2,3-triazole, obtained as an oil. (Compound 27)

EXAMPLE 28

Chlorine was bubbled through a stirred solution of compound 3 (5.45 g) in carbon tetrachloride (40 ml), over 5 hours, stood at room temperature for 16 hours and chlorine passed through for another 4½ hours. Solvent was evaporated and the residue purified by silica gel column chromatography to give 2-(2,6-dichloro-4-trifluoro-methylphenyl)-4-dichloromethylthio-5-methyl-2H-1,2,3-triazole, obtained as an oil, $N_D^{20}=1.5556$. (Compound 28)

EXAMPLE 29

Compound 1 (5.68 g) was stirred for 24 hours at room temperature with acetyl chloride (37 ml). Excess acetyl chloride was evaporated and the residue added to water extracted with ether and the extracts worked up to give 2-(2,6-dichloro-4-trifluoromethylphenyl)-4-chloro-5-methyl-2H-1,2,3-triazole, mp 100°–115°. (Compound 29)

EXAMPLE 30

In a similar manner to that described in one of the previous Example, the following compounds, were obtained.

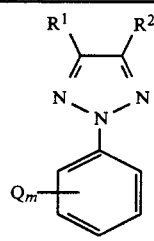

| Cpd | $Q_m$ | $R^1$ | $R^2$ | m.p. (°) |
|---|---|---|---|---|
| a | 2,6-Cl$_2$, 4-CF$_3$ | Me | SPh | 78 |
| b | 2,6-Cl$_2$, 4-CF$_3$ | Me | SEt | oil |
| c | 2,6-Cl$_2$, 4-CF$_3$ | Me | SCOMe | 113.5–114.5 |
| d | 2,6-Cl$_2$-4-CF$_3$ | Me | CH$_2$SPh | 81–85 |
| e | 2,4,6-Cl$_3$ | Me | SMe | 87.6–90 |
| f | 2,6-Br$_2$, 4-CF$_3$ | Me | SMe | 56–58 |
| g | 2,4-Br$_2$, 6-CF$_3$ | Me | SMe | oil |
| h | 2,3,4,5,6-F$_5$ | Me | SMe | oil |
| i | 2,3,5,6-F$_4$ | Me | SMe | 50–53 |
| j | 2,3,5,6-F$_4$, 4-CF$_3$ | Me | SMe | oil |
| k | 2,6-Cl$_2$, 4-CF$_3$S | Me | SMe | 58–60 |
| l | 2,3,5,6-F$_4$ | Me | OMe | oil[1] |
| m | 2,6-Cl$_2$, 4-CF$_3$ | Me | CH$_2$SMe | 67–68 |
| n | 2,6-Cl$_2$, 4-CF$_3$SO$_2$ | Me | SMe | 78.5–79.5 |

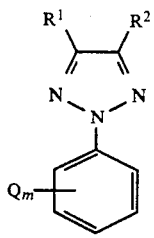

| Cpd | $Q_m$ | $R^1$ | $R^2$ | m.p. (°) |
|---|---|---|---|---|
| o | 2,6-Cl$_2$, 4-CF$_3$O | Me | SMe | oil |
| p | 2,6-Cl$_2$, 4-CF$_3$ | Me | CH$_2$SO$_2$Me | 67–68 |
| q | 2,6-Cl$_2$, 4-CF$_3$ | Me | SOMe | oil |
| r | 2,6-Cl$_2$, 4-CF$_3$ | Me | SCH$_2$F | oil[2] |
| s | 2,6-Cl$_2$, 4-CF$_3$ | CF$_3$ | CH$_2$SMe | 41–42 |
| t | 2,6-Cl$_2$, 4-CF$_3$ | Me | NMe$_2$ | 68–69 |
| u | 2,6-Cl$_2$-4-CF$_3$ | H | CH$_2$SCH$_2$Ph | 67–68 |
| v | 2,6-Cl$_2$-4-CF$_3$ | H | CH$_2$Sthien-2-yl | 76–77 |
| w | 2,6-Cl$_2$-4-CF$_3$ | H | CH=NOMe | 106–109 |
| x | 2,3,4,5,6-F$_5$ | Me | OMe | oil[3] |
| y | 2,6-Cl$_2$-4-CF$_3$ | Me | OMe | 64–66 |
| z | 2,4,6-Br$_2$ | Me | SMe | 78–80 |
| aa | 2,6-Cl$_2$, 4-CF$_3$ | H | CH$_2$SO$_2$Me | 192–193 |
| ab | 2,6-Cl$_2$, 4-CF$_3$ | H | CH$_2$SOMe | 140–142 |
| ac | 2,4,6-F$_3$ | Me | SMe | oil |
| ad | 2,6-Cl$_2$-4-CF$_3$ | H | CH=CH$_2$ | 69–70.5 |
| ae | 2,6-Cl$_2$-4-CF$_3$ | Me | morpholino | oil |
| af | 2,6-Cl$_2$-4-CF$_3$ | H | Bu$^t$ | 60–62 |
| ag | 2,6-Cl$_2$-4-CF$_3$ | Me | SBu$^t$ | 79–81 |
| ah | 2,6-Cl$_2$-4-CF$_3$ | Me | SPr$^i$ | oil |
| ai | 2,6-Cl$_2$-4-CF$_3$ | Me | pyrrolidino | oil |
| aj | 2,6-Cl$_2$-4-CF$_3$ | Me | piperidino | 67–70 |
| ak | 2,6-Cl$_2$-4-CF$_3$ | Me | SOCHCl$_2$ | oil |

[1] obtained as a by-product from preparation of i
[2] obtained from q using conditions similar to Example 10
[3] obtained as a by-product from preparation of h

EXAMPLE 31

Alkyl bromide (2.7 ml) and lithium hydroxide (0.76 g) were added to a stirred solution of Compound c (2.25 g) in tetrahydrofuran (110 ml). maintained under nitrogen and the mixture stirred under nitrogen for one day. It was then evaporated, water added and extracted with ether. The extract was worked up to give 4-alkylthio-2-(2,6-dichloro-4-trifluoromethylphenyl)-5-methyl-2H-1,2,3-triazole, mp 46°–18°. (Compound 31)

EXAMPLE 32

4-Bromomethyl-2-(2,6-dichloro-4-trifluoromethylphenyl)-2H-1,2,3-triazole (9.55 g), thiourea (2 g) and ethanol (100 ml) were heated under reflux for 4 hours. Solvent was removed and the residue washed with ether/hexane (1:1) to give S-[2-(2,6-dichloro-4-trifluoromethylphenyl)-2H-1,2,3-triazol-4-ylmethyl]isothiouronium bromide. m.p. 275°–277°. (Compound 32)

EXAMPLE 33

Sodium hydride (0.22 g of 80% suspension in oil) was added to a stirred solution of Compound 33 (2.2 g) in dimethylformamide (50 ml) maintained under nitrogen at 0° and the mixture stirred under nitrogen for 15 minutes. Dibromodifluoromethane (1.76 g) was added and the mixture stirred under nitrogen at room temperature for 20 hours. It was then poured into water, extracted with ether and the extract worked up to give 2-(2,6-dichloro-4-trifluoro-methylphenyl)-4-bromodifluoromethylthio-5-methyl-2H-1,2,3-triazole, mp 46°–48°. (Compound 33)

EXAMPLE 34

2-(2,6-Dichloro-4-trifluoromethylphenyl)-4-mercapto 5-methyl-2H-1,2,3-triazole was treated with chlorodifluoromethane in a similar manner to Example 22 to give 2-(2,6-dichloro-4-trifluoromethylphenyl)-4-difluoro-methylthio-5-methyl-2H-1,2,3-triazole, m.p. 33°–35°. (Compound 35)

EXAMPLE 35

2-(2,6-dichloro-4-ethoxycarbonylphenyl)-4-methyl-2H-1,2,3-triazole 1-oxide (2 g) was treated with trimethyloxonium tetrafluoroborate in a similar manner to Example 2. The product was dissolved in tetrahydrofuran and and treated as in Example 3 with sodium methanethiolate (0.4 g) to give 2-(2,6-dichloro-4-ethoxycarbonylphenyl)-4-methyl-2H-1,2,3-triazole, m.p. 136°–137.5°. (Compound 35)

EXAMPLE 36

A mixture of Compound 24 (2 g) in tetrahydrofuran (50 ml) and n-butyllithium (3.4 ml) was stirred at −78° for 1 hour. The mixture was quenched with water, solvent evaporated and extracted with ether. The extract was worked up to give 4-acetylenyl-2-(2,6-dichloro-4-trifluoro-methylphenyl)-2H-1,2,3-triazole, m.p. 85°–86°. (Compound 36)

EXAMPLE 37

This example illustrates an alternative process for preparing the compound of Example 3.

N-Chlorosuccinimide (7.3 g) was added, portionwise, to a solution of 2-oxopropanal 1-oxime (4.8 g) in dimethylformamide (30 ml). The reaction was heated to 50° and hydrochloric acid gas bubbled through to initiate the reaction. The mixture was then stirred at room temperature for an hour. Poured into water, extracted with ether and the extracts worked up to give crude 1-chloro--oxopropanal 1-oxime. This (1.5 g) in dimethylformamide (25 ml) was then reacted with sodium methanethiolate (0.86 g). After 5 hours at below 5°, the mixture was poured into water and extracted with ether and the extracts worked up to give crude 1-methylthio-oxopropanal 1-oxime. This (1.0 g) was then reacted with 2,6-dichloro-4-trifluoromethylphenylhydrazine (1.84 g), in a similar to that described in Example 1, to give 2-(2,6-dichloro-4-trifluoromethylphenylhydrazono)-methylthiopropanal-1-oxime. This (1.4 g) was then reacted with acetic anhydride, in a similar manner to Example 5, to give 2-(2,6-dichloro-4-trifluoromethylphenylhydrazono)-1-methylthiopropanal 1-acetyloxime. This (1.4 g) was then stirred with a mixture of caesium carbonate (1.1 g) and tetrahydrofuran (40 ml) at room temperature for 2 hours. Solvent was removed and the residue worked up to give compound 3.

EXAMPLE 38

In a similar manner to Example 37, there was obtained 2-(3-chloro-5-trifluoromethyl-2-pyridyl)-4-methyl-methylthio-2H-1,2,3-triazole. (Compound 37)

PREPARATION OF STARTING MATERIALS AND COMPOUNDS USED ONLY AS INTERMEDIATES

A mixture of 2,6-dichloro-4-trifluoromethylphenylhydrazine (34 g), 2-oxopropanedial 1,3-dioxime (17 g) and ethanol (300 ml) was heated under reflux for 3½ hours. The solvent was evaporated under reduced pressure and the residue triturated with light petroleum (bp 40°-60°) and filtered to give 2-oxopropanedial 2-(2,6-dichloro-4-trifluoromethylphenylhydrazone) 1,3-dioxime. This product (36 g) was stirred in acetic anhydride (350 ml) and acetic acid (220 ml) at room temperature for 45 mins. The mixture was poured into water and filtered and the residue dried in vacuo at 40° to give 2-oxopropanedial 1-acetyloxime 2-(2,6-dichloro-4-trifluoromethylphenylhydrazone) 3-oxime.

A mixture of this product (38.5 g) and caesium carbonate (32.6 g) in tetrahydrofuran (1000 ml) was stirred at room temperature for 1 hour. The mixture was stirred at room temperature for 1½ hours. The solvent was evaporated under reduced pressure and the residue taken up in ether. The extract was washed with water, dried and evaporated. The residue was triturated with light petroleum (bp 40°-60°) and filtered to give 2-(2,6-dichloro-4-trifluoro-methylphenyl)-2H-1,2,3-triazole-4-carboxaldehyde oxime. A mixture of 2-(2,6-dichloro-4-trifluoromethylphenyl)-5-methyl-2H-1,2,3-triazol-4-ylmethanol (4.1 g), hydrobromic acid (10 ml of 48%) and concentrated sulphuric acid (1ml) was heated under reflux for 10 minutes. The mixture was added to water and extracted with ether. The extract was worked up to give 4-bromomethyl-2-(2,6-dichloro-4-trifluoromethylphenyl)-5-methyl-2H-1,2,3-triazole, m.p. 98°-100°. Compound 6 (5 g), isopropanol (50 ml) and methanol (20 ml) was added sodium borohydride (0.67 g), portionwise. The mixture was stirred at room temperature overnight. Water was added and the mixture made acidic with hydrochloric acid. The mixture was extracted with ether and the extract washed with brine dried and evaporated to give [2-(2,6-dichloro-4-trifluoromethylphenyl)-2H-1,2,3-triazol-4-yl]methanol, mp 87°-88°.

To a mixture of this alcohol (0.5 g) and triethylamine (0.22 ml) in tetrahydrofuran (10 ml) was added, dropwise. methanesulphonyl chloride (0.18 g). The mixture was stirred for 40 minutes, poured into water and extracted with ether. The extract was dried and evaporated and the residue triturated with light petroleum (bp 40°-60°) to give [2-(2,6-dichloro-4-trifluoromethylphenyl)-2H-1,2,3-triazol-4-yl]methyl methanesulphonate, mp 96°-97°.

In a similar manner:
[2-(2,6-dichloro-4-trifluoromethylphenyl)-5-methyl-2H-1,2,3-triazol-4-yl]methanol gave [2-(2,6-dichloro-4-trifluoromethylphenyl)-5-methyl-4-2H-1,2,3-triazol-4-yl]methyl methanesulphonate, mp 126°-127°.

[2-(2,6-Dichloro-4-trifluoromethylphenyl)-2H-1,2,3-triazol-4-yl]methanol was converted to 4-bromomethyl-2-(2,6-dichloro-4-trifluoromethylphenyl)-2H-1,2,3-triazole. in a similar manner to above.

2-(2,6-dichloro-4-trifluoromethylphenyl)-2H-1,2,3-triazole-4-carboxaldehyde (1 g) was oxidised using chromium trioxide (26.67 g) in water (40 ml) and concentrated sulphuric acid (23 ml), made up to 100 ml. The product was extracted with ether and worked up in conventional manner to give 2-(2,6-dichloro-4-trifluoromethylphenyl)-2H-1,2,3-triazole-4-carboxylic acid, m.p. 155°-157°.

2,6-Dichloro-4-trifluoromethylphenylhydrazine was reacted with 2,3-dioxobutyranilide 2-oxime, in a similar manner to above to give 2,3-dioxobutyranilide 3-(2,6-dichloro-4-trifluoromethylphenylhydrazone) 2-oxime, m.p. 185°-186°. This was then treated with acetic anhydride in acetic acid to give 2,3-dioxobutyranilide 2-acetyloxime 3-(2,6-dichloro-4-trifluoromethylphenylhydrazone). This was cyclised with caesium carbonate to give 2-(2,6-dichloro-4-trifluoromethylphenyl)-5-methyl-2H-1,2,3-triazole-4-carboxanilide, m.p. 185°-186°.

A mixture of this (15.35 g), triethylamine (5.2 ml). di-tert-butyl carbonate (16.2 g) and 4-(dimethylamino)-pyridine (4.53 g) in dichloromethane (250 ml) was stirred at room temperature for 3 hours. The mixture was evaporated and tetrahydrofuran added to the residue. Lithium hydroxide (6 g in 100 ml water) was added and the mixture was stirred at room temperature for 7 hours. The mixture was evaporated and the residue taken up in water and acidified. The solid was collected and extracted with ether and the extracts worked up to give 2-(2,6-dichloro-4-trifluoromethylphenyl)-5-methyl-2H-1,2,3-triazole-4-carboxylic acid, m.p. 185°-186°. A suspension of this acid (9 g) in ether was reduced with diisobutylaluminium hydride (0.11 mole) to give crude [2-(2,6-dichloro-4-trifluoromethylphenyl)-5-methyl-2H-1,2.3-triazol-4-yl]methanol, obtained as oil which solidified on standing.

This was treated with methanesulphonyl chloride in a similar manner as described above to give 2-(2,6-dichloro-4-trifluoromethylphenyl)-5-methyl-2H-1,2,3-triazol-4-yl-methyl methanesulphonate, mp 126°-128°.

Aqueous sodium hydroxide (250 ml of 0.2 N solution) was added to a stirred solution of Compound c (9.4 g) in tetrahydrofuran (100 ml), maintained under nitrogen and the mixture stirred under nitrogen for 45 minutes. It was then evaporated, water added and extracted with ether. The aqueous layer was acidified and also extracted with ether. The combined extracts were worked up to give 2-(2,6-dichloro-4-trifluoromethylphenyl)-4-mercapto-5-methyl-2H-1,2,3-triazole, mp 86°-89°.

FORMULATION EXAMPLE

This example illustrates typical concentrates that can be formulated from compounds of the invention.
(a) Wettable powder
  Compound of the invention 25% w/w
  Sodium lignosulphonate 5% w/w
  Silica 10% w/w
  China clay 60% w/w
(b) Emulsifiable concentrate
  Compound of the invention 100 g/l
  Calcium dodecylbenzenesulphonate 50 g/l
  Castor oil ethoxylate 50 g/l
  Aromatic solvent (Solvesso 200) 823 g/l

TEST EXAMPLE (1) Ticks (*Boophilus microplus*)

(a) Larval test
Filter papers (9 cm diameter) were impregnated with 1 ml aliqots of acetone solutions or suspensions of test compound at various concentrations. The papers were allowed to dry and then folded into envelopes in which approximately 50 cattle tick larvae, (*Boophilus microplus*) were enclosed and held at 25° C. and >80% R. H. for 48 hours,. The percentage mortality of tick larvae was then recorded and compared with controls. The controls gave less than 5% mortality whereas compounds 1-2, 5, 8, 11-13, 18, 20-23, 25, 27, 28, 31, 33, 34, b, c, e, f, k, m, o, p, r, t, v, aa, ab, ah and ak had an $LD_{50}$ of less than 300 ppm.

(b) Female injection test

Test compounds were dissolved in a suitable solvent to a desired concentration. Using a microapplicator, 2 microlitres of the solution were injected into the blood filled stomach of a tick (Boophilus microplus), 5 replicate ticks were treated at each concentration and subsequently each tick is retained separately in partitioned petri dish held at 25° C. and >80% R.H., until mortality of ticks or fecundity and viability of eggs produced by survivors could be assessed. The percentage reduction in total reproductive capacity (i.e, the combined effects of adult mortality, reduced fecundity and mortality of eggs) was then recorded and compared with controls. The controls gave less than 5% reduction of reproductive capacity whereas compounds 2, 3, 5, 11. 13, 15, 20, a, b, d, e, j, m and u gave at least 50% reduction of reproductive capacity at a concentration of 50 microgram/tick or less.

(2) Sheep blowfly (Lucilia sericata)

1 ml aliquots of acetone solutions or suspensions, containing test compound at various concentrations, were applied to cotton wool dental rolls (1 cm×2 cm). contained in glass vials 2 cm diameter×5 cm long. After drying, the treated materials were then impregnated with 1 ml of nutrient solution, infested with approximately 30 first instar larvae of sheep blow fly (Lucilia sericata). closed by a cotton wool plug and held at 25° C. for 24 hours. For the controls the mortality was <5% whereas compounds 2, 3, 5, 7, 8, 10, 12, 13, 15, 16, 18–20, 22, 28, 31, 33, e, f, g, k, m, o, p, q, r, s, t, w, y, aa, ab and ac had an $LC_{50}$ of less than 300 ppm.

(3) House fly (Musca domestica)

Aliquots (0.7 ml) of acetone solutions or suspensions of test compounds at various concentrations were applied to filter papers (9 cm diameter) placed in the bottom of petri dishes (9 cm diameter) closed by glass lids. After evaporation of solvent, the treated surfaces, together with controls treated with acetone alone, were then infested with adult houseflies. (Musca domestica) and held at 22° C. for 24 hours. The percentage mortality of the insects was then recorded. Less than 5% mortality resulted in the controls whereas the $LD_{50}$ of compounds 1–5, 7–13, 17–22, 25, 26, 28, 28, 29, 31, 33, 34, b, e, f, g, h, i, j, k, 1, m, n, o, p, q, r, s, t, w, x, y, aa, ab, ac, ad. ae, af, agf, ah, ai, aj and ak was less than 1000 mg/m².

(4) Cockroach (Blattella germanica)

Aliquots (1 ml) of solutions or suspensions of test compounds in a suitable solvent at various concentrations were applied to glass plates (10 cm×10 cm). After evaporation of solvent, the treated surfaces, together with controls treated with solvent alone, were then infested with approximately 10 first instar nymphs of the German cockroach. (Blattella qermanica), retained on the treated surface within pTFE-coated glass rings 6 cm in diameter and held for 24 hours at 25° C. The percentage mortality of the insects was then recorded. Less than 5% mortality resulted in the control treatments whereas the $LD_{50}$ of compounds 3, 5, 11–13, 18, 20, b, k and r was less than 100 mg/m².

(5) Yellow fever mosquito (Aedes aeqypti)

Aliquots (1 ml) of acetone solutions or suspensions of test compounds at various concentrations were applied to 1 g portions of wholemeal flower. Small quantities (c. 10–12 mg) were added daily to crystallising dishes containing distilled water (100 ml) and 10–14 newly T hatched larvaae of A, aeqypti. Daily feeding was maintained until the mosquitoes pupated. The dishes were maintained at 25° C., when all untreated controls had emerged, the percentage mortality is assessed using the equation $$\% \text{ mortality} = 100 - \frac{(\text{No of live adults} + \text{pupae}) \times 100}{(\text{total pupae} + \text{adults})}$$

Less than 5% mortality resulted in the control treatments whereas the $LD_{50}$ of compounds 2 and 3 was less than 1000 ppm parts of flour.

(6) Brown rice hoppers (Nilaoarvata lugens Stal)

In a heated greenhouse rice seedlings (about 15 per pot) were grown until formation of the third leaf and then sprayed until dripping wet with an aqueous preparation of the test compound. After drying the sprayed leaves, a transparent cylinder was placed over each pot. 30 Adult brown rice-hoppers (Nilaparvata lugens) were introduced into each pot. After 2 days at 26° C. in the greenhouse, the amount of dead hoppers was determined. Compounds 1, 2, 3, 5, 7, 10–13, 18, 20 m. P, q, and w had an $LC_{90}$ of less than 160 ppm.

(7) Pre-Emergence herbicide test

In a greenhouse, the noted plant species were treated pre-emergency with the noted compounds of the invention. at the rate shown. The compounds of the invention were sprayed evenly over the vessels containing seeds of the plants as an aqueous acetone solution containing a wetting agent. After 3 to 4 weeks growth, the plants were visually assessed for any herbicidal response.

At least 70% control of the noted weeds, at a rate of 3kg/ha or less, was shown by following compounds
  lyqonum lapathifolium 8, 12, 15
  Galium aparine 15
  Chrysanthemum seqetum 15
  Alopecurus myosuroides 15
  Avena fatua 15
  Abutilon theophrasti 9, 12, 15, 16
  Pharbitis purpurea 15
  Echinochloa crus-galli 15
  Setaria viridis 15
  Solanum nigrum 9,15

(8) post-Emergence herbicide test

In a greenhouse, seedlings of the noted plant species were treated post-emergently with the noted compounds of the invention, at the rate shown. The compounds of the invention were sprayed evenly over the vessels containing the plants as an aqueous acetone solution containing a wetting agent. After 3 to 4 weeks growth, the plants were visually assessed for any herbicidal response.

At least 70% control of the noted weeds, at a rate of 3 kg/ha or less, was shown by following compounds:
  Polygonum lapathifolium 6, 8, 12, 14, 15
  Galium aparine 8, 15
  Chyrsanthemum segetum 15
  Alopecurus myosuroides 12, 15
  Avena fatua 15
  Abutilon theophrasti 9, 12, 15
  Pharbitis purpurea 8, 14, 15
  Echinochloa crus-galli 8, 15
  Setaria viridis 8, 15
  Solanum nigrum 8, 14

We claim:

1. A compound of formula I

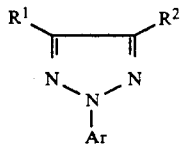

in which

Ar is 2,6-dichloro-4-trifluoromethylphenyl;

$R^1$ is hydrogen or methyl, and $R^2$ is halogen, nitro, cyano, alkylthio, haloalkylthio, alkylsulphonyl, alkylsulphinyl, halomethyl, haloalkythiomethyl or alkylthiomethyl, in which any alkyl moiety of a group which contains alkyl has 1 to 4 carbon atoms.

2. A compound according to claim 1, in which $R^2$ is nitro, haloalkylthio, alkylthio or alkylthiomethyl.

3. A compound according to claim 2 in which $R^1$ is hydrogen and $R^2$ is methylthiomethyl.

4. A composition which comprises an effective amount of a compound of formula I

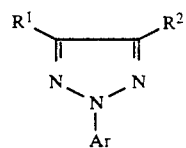

in which

Ar is 2,6-dichloro-4-trifluoromethylphenyl;

$R^1$ is hydrogen or methyl, and $R^2$ is halogen, nitro, cyano, alkylthio, haloalkylthio, alkylsulphonyl, alkylsulphinyl, halomethyl halo alkylthiomethyl or alkylthiomethyl, in which any alkyl moiety of a group which contains alkyl has 1 to 4 carbon atoms, said compound being in admixture with an agriculturally acceptable diluent or carrier.

5. A composition according to claim 4 in which $R^1$ is hydrogen and $R^2$ is methylthiomethyl.

6. A composition according to claim 4 in which $R^2$ is nitro, haloalkylthio, alkyltion, or alkylthiomethyl.

7. A method of combatting insects or acarids at a locus infested or liable to be infested therewith, which comprises applying to the locus an effective amount of a composition of formula I, as defined in claim 4.

8. A method of combatting insects or acarids, at a locus an effective amount of infested or liable to be infested therewith, which comprises applying to the locus a composition of formula I, as defined in claim 5.

9. A method of combatting insects or acarids at a locus an effective amount of infested or liable to be infested therewith, which comprises applying to the locus a composition of formula I, as defined in claim 6.

* * * * *